United States Patent [19]

Harreld et al.

[11] Patent Number: 5,186,322

[45] Date of Patent: Feb. 16, 1993

[54] SPONGE CARRIER AND COUNTER

[75] Inventors: Donald R. Harreld, Woodstock; Barbara T. Skiba, Chicago, both of Ill.

[73] Assignee: Sage Products, Inc., Crystal Lake, Ill.

[21] Appl. No.: 869,042

[22] Filed: Apr. 14, 1992

Related U.S. Application Data

[63] Continuation of Ser. No. 456,949, Dec. 26, 1989, abandoned.

[51] Int. Cl.$^5$ .............................................. A61B 19/00
[52] U.S. Cl. .................................... 206/216; 206/440; 206/459; 206/459.5; 2/159; 383/74; 383/75; 294/1.3; 128/DIG. 24
[58] Field of Search ............... 206/278, 438, 216, 440, 206/459; 2/161 R, 167, 168, 162, 159; 383/74, 71, 75; 294/1.3, 25; 128/DIG. 24

[56] References Cited

U.S. PATENT DOCUMENTS

| | | | |
|---|---|---|---|
| 1,457,858 | 6/1923 | Ruddell | 2/159 X |
| 2,670,473 | 3/1954 | Stebic | 2/159 |
| 2,783,759 | 3/1957 | Hill | 2/159 X |
| 4,215,886 | 8/1980 | Naderi et al. | 294/1.3 |
| 4,515,841 | 5/1985 | Dyke | 294/1.3 X |
| 4,658,444 | 4/1987 | Figlia et al. | 2/161 R |
| 4,677,697 | 7/1987 | Hayes | 294/1.3 X |
| 4,741,565 | 5/1988 | Bagg | 294/1.3 |
| 4,788,733 | 12/1988 | Lerner | 294/1.3 X |
| 4,845,781 | 7/1989 | Strickland et al. | 294/1.3 X |
| 4,876,747 | 10/1989 | Coffey et al. | 2/168 |

FOREIGN PATENT DOCUMENTS 2215425 7/1973 Fed. Rep. of Germany.

Primary Examiner—Jimmy G. Foster
Assistant Examiner—Jacob K. Ackun, Jr.
Attorney, Agent, or Firm—Lee, Mann, Smith, McWilliams, Sweeney & Ohlson

[57] ABSTRACT

A surgical sponge carrier and counter formed from a pliable film. The carrier and counter includes a glove-like portion with a tubular sleeve extending therefrom. A closure is located in the sleeve, the closure comprising a drawtape disposed in a guide and secured at one location to the sleeve. A notch is located in the guide generally opposite the location at which the drawtape is secured to the sleeve, the drawtape extending into the notch and forming a loop which may be engaged for both removal of the sponge carrier and counter by turning it inside out about the glove-like portion, and also drawing the now-inside out carrier and counter closed about its contents.

14 Claims, 1 Drawing Sheet

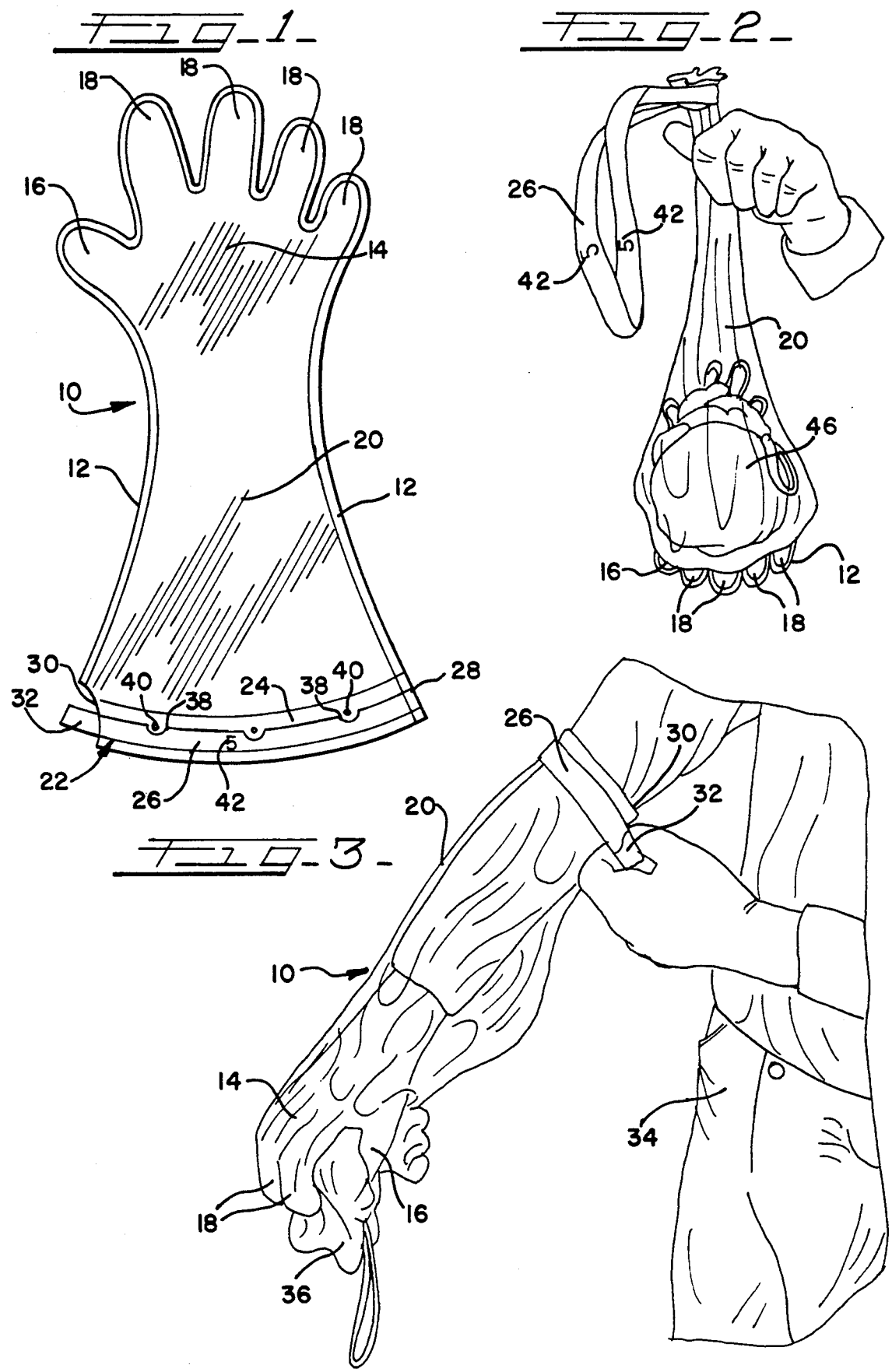

SPONGE CARRIER AND COUNTER

This application is a continuation, of application Ser. No. 456,949, filed Dec. 26, 1989, now abandoned.

BACKGROUND OF THE INVENTION

This invention relates to surgical sponge counters, and in particular to a glove-like surgical sponge carrier and counter which is worn by the user and, when ready for disposal, is turned inside out about the hand of the user to contain sponges or other items gripped by the user.

Surgical sponges used in all surgical operations are typically packaged in containers having 5 to 10 sponges therein. As the sponges are used in the operating room, they are collected for later counting, as an accurate count of the number of sponges is critical to assure that nothing is left behind in an incision, before it is closed.

During surgury, for accounting for used sponges, the nurse or nurses assisting in the operation count the used sponges as time allows, and then collect the counted sponges in many ways, such as in plastic bags, in bundles of 5 or 10 sponges tied together, or in special devices used for counting of sponges. Many different types of special devices have been developed, the following U.S. patents merely being examples: U.S. Pat. Nos. 3,613,899; 3,749,237; 3,948,390; 4,190,153; 4,312,447; 4,422,548; 4,429,789; 4,784,267; and 4,832,198.

When a surgical procedure is completed, the doctor requests that the total number of sponges used be accounted for. The nurses check their counts to see how many sponges have been used and whether the number used equals the number actually employed during the operation. If so, the incision is sewn and the operation is completed.

If, on the otherhand, not all sponges have been accounted for, a recount is requested, and all sponges must be counted one-by-one before the surgical incision is closed. When using one of the prior art sponge counters as identified above, this procedure is somewhat accelerated, but the sponge counters themselves are complicated and therefore expensive devices.

Gloves or mits which may be turned inside out after use have previously been developed. U.S. Pat. Nos. 4,677,697 and 4,788,733 depict such devices. While such devices are relatively simple and may readily be turned inside out, in order to close the inside out glove, two hands must be used to separately draw a pull tie and tie the pull tie to close the bag-like inside out glove structure.

SUMMARY OF THE INVENTION

The present invention is directed to a surgical sponge carrier and counter which is formed from a pliable film and which may be turned inside out after use. The sponge carrier and counter includes a glove portion including a thumb portion and a fingers portion. A tubular sleeve portion extends form the glove portion, and a closure is located in the sleeve portion. The closure includes a circumferential drawtape guide formed in the sleeve portion and spaced from the glove portion, with a continuous drawtape disposed in the guide, the drawtape being secured at one location to the sleeve and being slideable in the guide except at the one location. An engagement notch is formed in the guide in registration with the thumb portion, the notch being generally opposite the location of attachment of the drawtape to the sleeve. The drawtape extends into the notch and forms a loop in the notch for engagement by the user of the drawtape. This facilitates removal of the sponge carrier and counter from the arm of the user by engagement of the drawtape loop in the notch and then turning the sponge carrier and counter inside out about the glove portion and, continuing in the same action, closing the now-inside out sponge carrier and counter by pulling further on the drawtape.

In accordance with the preferred form of the invention, the guide for the drawtape is located at one end of the sleeve portion. The guide may be a channel or other suitable means formed at the one end of the sleeve portion to contain and direct the drawtape.

It is preferred that the engagement notch be in alignment with the thumb portion. As used in the context of the present application, the term "alignment" is intended to mean accessible to the other hand of the user when the carrier and counter is worn on one hand. It has been determined that location of the notch at any position from that in direct alignment with the thumb portion to a position approximately 90° along the circumference of the sleeve portion in either direction from direct alignment is still readily accessible to the user. In other words, location of the engagement notch along a 180° arc, extending 90° in either direction from direct alignment with the thumb portion, will produce an acceptable location for the engagement notch.

Normally, when the drawtape is pulled, there is enough frictional interference between the drawtape and the channel in which it is located so that the closed carrier and counter remains closed. However, in addition, one form of the invention includes means for temporarily retaining the drawtape in the guide when the drawtape has been pulled. That means can include at least one tack seal in the guide and at least one indentation in the drawtape, with the indentation engaging the tack seal when the drawtape is pulled.

The film forming the carrier and counter of the invention is generally transparent, and in order to properly identify the carrier and counter and its contents, indicia may be included on the drawtape visible through the film. Preferably, the indicia at least includes a number identifying the number of sponges contained by the carrier and counter after it has been turned inside out.

BRIEF DESCRIPTION OF THE DRAWING

The invention is described in greater detail in the following description of examples embodying the base mode of the invention, taken in conjunction with the drawing figures, in which:

FIG. 1 is an elevational view of a sponge carrier and counter according to the invention, including a modification of the drawtape;

FIG. 2 is a schematic illustration of the carrier and counter according to the invention after it has been turned inside out about gripped sponges, and after the drawtape has been pulled to close the container formed by the inside out sponge carrier and counter; and FIG. 3 is a schematic illustration of deployment of the sponge carrier and counter, and showing initial gripping of the drawtape for removal of the sponge carrier and counter from the wearer, with the subsequently removed carrier and counter having been illustrated in FIG. 2.

DESCRIPTION OF EXAMPLES EMBODYING THE BEST MODE OF THE INVENTION

A sponge carrier and counter according to the invention is generally designated at 10 in the drawing figures. The carrier and counter 10 is made from a pliable film in a glove-like configuration, comprising two identical sheets of film which have been heat sealed along a heat seal 12 about the periphery of the carrier and counter 10. The carrier and counter 10 may be worn on either hand of the user, as will be explained in greater detail below.

The carrier and counter 10 includes a glove portion 14 including a thumb portion 16 and a fingers portion formed from four digits 18. Sizing of the thumb portion 16 and digits 18 is adequate to accomodate all users, a single size of the sponge carrier and counter 10 fitting all users. The individual digits 18 permit easy counting of sponges by permitting sponges to be held between the fingers.

A tubular sleeve portion 20, formed by the opposite heat seals 12, extends from the glove portion 14, and terminates at a closure 22. The closure 22 includes a circumferential drawtape guide 24 formed at one end of the sleeve portion 20, the guide 24 simply being a folded-over part of the ends of the sleeve portion 20 that has been tack sealed or otherwise secured so that a channel is formed for passage of a drawtape 26. The drawtape 26, in turn, comprises a continuous flat tape lodged in the channel 24, and secured at one location 28, preferably by the heat seal 12, to the sleeve 20. The drawtape 26 is therefore slideable in the tubular guide 24 formed in the opposite sides of the sleeve portion 20 with the exception of the location 28 at which the drawtape is secured.

An engagement notch 30 is formed in the guide 24 in alignment with the thumb portion 16. As best shown in FIG. 1, the notch 30 is generally opposite the location 28, and the drawtape 26 extends into the notch 30, forming a loop 32 in the notch for engagement of the drawtape 26 for removal of the sponge carrier and counter 10 from the user's arm. Thus, the drawtape 26 extends from the location 28 through the drawtape guide 24 in one side of the sleeve 20, emerging at the notch 30 to form the loop 32, and then extending through the drawtape guide in the opposite side of the sleeve 20 to the location 28, completing the continuous extent of the drawtape 26.

In use, the sponge carrier and counter is worn by the user on either arm. As shown in FIG. 3, the carrier and counter 10 is worn on the right arm of a user 34, the user having a series of sponges 36 gripped in the glove portion 14. When a desired number of sponges are gripped, the user engages the extending loop 32 with the opposite hand (the left hand in FIG. 3), and pulls downwardly on the loop 32 toward the gloved (right) hand, while continuing to grip the sponges 36. The user then pulls the carrier and counter 10 inside out over the gripped sponges 36, and continues to pull the drawtape 26 while gripping the sponges in order to pull the drawtape closed, into the orientation shown in FIG. 2 with the now-inside sponge carrier and counter 10 having the sponges 16 contained therewithin.

The preferred form of the invention is shown in FIG. 1, with the notch 30 in direct alignment with the thumb portion 16 so that the user 34 may readily engage the loop 32 with the opposite hand, as shown in FIG. 3. However, the notch can be located at other than in direct alignment with the thumb portion 16, and as explained above, the notch 30 can be located as much as 90° or more displaced from the orientation shown in FIGS. 1 and 3. If the notch is located atop or beneath the arm when the sponge carrier and counter 10 is worn, it is still readily engagable by the other hand of the user. However, location of the notch much beyond such a location makes removal of the sponge carrier and counter 10 by the loop 32 quite awkward, and impossible for some users.

When the sponge carrier and counter 10 is removed and turned inside out as shown in FIG. 2, and with the drawtape 26 pulled closed, the drawtape 26 may be knotted or otherwise affixed so that the sponge carrier and counter 10 forms a closed pouch for the used sponges 36. In order to aid in maintaining the sponge carrier and counter 10 closed before the drawtape 26 is tied, the drawtape 26 may include one or more indentations 38 in alignment with and engaging one or more tack seals 40 in the guide 24. While the drawtape 26 and indeed the entire structure of the carrier and counter 10 is preferably pliable plastic, additional frictional interengagement of the indentations 38 and tack seals 40 can help retain the inverted carrier and counter 10 closed when once removed.

As explained above, it is important that an accurate count be kept of the number of sponges 36 used during an operation. To aid in that count, the sponge carrier and counter 10 can be designated to hold a certain number of sponges 36. That number can be included as indicia 42 printed on the drawtape 26 so that when the drawtape 26 is drawn, the indicia 42 remains visible to identify the contents.

As depicted schematically in the drawing figures, the sponge carrier and counter 10 is both removed and closed in a single operation using a single hand. This greatly simplified and facilitates use of the sponge carrier and counter 10.

The invention can be modified in many respects. As explained above, the indentations 38 and tack seals 40 need not be used, nor need written indicia 42 be employed on the drawtape 26, since the drawtape 26 can be colored or otherwise coded to designate the quantity of sponges or other items carried by the inside out sponge carrier and counter 10. Also, while the notch 30 is preferably opposite the location 28 at which the drawtape 26 is secured to the sleeve 20, the orientation of the notch 30 need not be directly opposite the location 28. Various other changes may be made to the invention without departing from the spirit thereof or scope of the following claims.

What is claimed is:

1. A surgical sponge carrier and counter formed from a pliable film and comprising
   a. a glove portion including a thumb portion and a fingers portion,
   b. a tubular sleeve portion extending from said glove portion, and
   c. a closure located in said sleeve portion, said closure comprising
      i. a circumferential drawtape guide formed in said sleeve portion and spaced from said glove portion,
      ii. a continuous drawtape disposed in said guide, said drawtape being secured at one location to said sleeve and being slidable in said guide except at said one location, said one location being generally opposite said thumb portion, iii. an engagement notch in said guide in alignment with said thumb portion, said notch being generally opposite said one location, and said drawtape extending into said notch and forming a loop in said notch for engagement of said drawtape and removal of the sponge carrier and counter by turning the sponge carrier and counter inside out about said glove portion, and iv. means for temporarily retaining said drawtape at a location in said guide to maintain the carrier and counter closed, said means for temporarily retaining being located within said guide and engaging said drawtape within said guide.

2. A surgical sponge carrier and counter according to claim 1 in which said guide is located at one end of said sleeve portion.

3. A surgical sponge carrier and counter according to claim 1 in which said guide is a channel in said sleeve portion.

4. A surgical sponge carrier and counter according to claim 1 in which said means for temporarily retaining comprises at lest one tack seal in said guide and at least one indentation in said drawtape engaging said tack seal.

5. A surgical sponge carrier and counter according to claim 1 in which said film is generally transparent, and including indicia on said drawtape visible through said film.

6. A surgical sponge carrier and counter according to claim 5 in which said indicia includes a number identifying a number of sponges contained by the carrier and counter.

7. A surgical sponge carrier and counter according to claim 1 in which said fingers portion comprises individual finger digits.

8. A surgical sponge carrier and counter formed from a pliable film and comprising a. a glove portion including a thumb portion and a fingers portion, b. a tubular sleeve portion extending from said glove portion, c. a closure located in said sleeve portion, said closure comprising i. a circumferential drawtape guide formed in said sleeve portion and spaced from said glove portion, ii. a continuous drawtape disposed in said guide, said drawtape being secured at one location to said sleeve and being slidable in said guide except at said one location, said one location being generally opposite said thumb portion, and iii. an engagement notch in said guide in alignment with said thumb portion, said notch being generally opposite said one location, and said drawtape extending into said notch and forming a loop in said notch for engagement of said drawtape and removal of the sponge carrier and counter by turning the sponge carrier and counter inside out about said glove portion, and d. said film being generally transparent, and including indicia on said drawtape visible through said film.

9. A surgical sponge carrier and counter according to claim 8 in which said guide is located at one end of said sleeve portion.

10. A surgical sponge carrier and counter according to claim 8 in which said guide is a channel in said sleeve portion.

11. A surgical sponge carrier and counter according to claim 8 including means for temporarily retaining said drawtape at a location in said guide to maintain the carrier and counter closed.

12. A surgical sponge carrier and counter according to claim 11 in which said means for temporarily retaining comprises at least one tack seal in said guide and at least one indentation in said drawtape engaging said tack seal.

13. A surgical sponge carrier and counter according to claim 8 in which said indicia includes a number identifying a number of sponges contained by the carrier and counter.

14. A surgical sponge carrier and counter according to claim 8 in which said fingers portion comprises individual finger digits.

* * * * *